US005488034A

United States Patent [19]

McGregor et al.

[11] Patent Number: 5,488,034
[45] Date of Patent: Jan. 30, 1996

[54] PHARMACEUTICAL COMPOSITION COMPRISING BPI PROTEINS

[75] Inventors: Weldon C. McGregor, Los Angeles; James Stubstad, Lafayette; C. Paul Chang, Chatsworth, all of Calif.

[73] Assignee: XOMA Corporation, Berkeley, Calif.

[21] Appl. No.: 190,869

[22] Filed: Feb. 2, 1994

Related U.S. Application Data

[63] Continuation-in-part of Ser. No. 12,360, Feb. 2, 1993, abandoned.

[51] Int. Cl.$^6$ ............................ A61K 35/14; A61K 38/16
[52] U.S. Cl. ............................ 514/12; 514/21; 530/350
[58] Field of Search ..................... 514/12, 21; 530/350

[56] References Cited

U.S. PATENT DOCUMENTS

| | | | |
|---|---|---|---|
| 3,839,314 | 10/1974 | Fekete et al. | 424/11 |
| 4,478,829 | 10/1984 | Landaburu et al. | 424/177 |
| 4,719,239 | 1/1988 | Muller et al. | 514/785 |
| 4,933,179 | 6/1990 | Allison et al. | 424/89 |
| 5,030,448 | 7/1991 | Hunter | 424/83 |
| 5,037,664 | 8/1991 | Shaked et al. | 424/85.2 |
| 5,039,520 | 8/1991 | Hunter | 424/83 |
| 5,041,288 | 8/1991 | Hunter | 424/83 |
| 5,071,649 | 12/1991 | Hunter | 424/78.38 |
| 5,096,885 | 3/1992 | Pearlman et al. | 514/12 |
| 5,118,528 | 6/1992 | Fessi et al. | 424/485 X |
| 5,118,794 | 6/1992 | Grangeorge et al. | 530/363 |
| 5,133,908 | 7/1992 | Stainmesse et al. | 424/485 X |
| 5,152,979 | 10/1992 | Hunter | 424/78.38 |
| 5,182,106 | 1/1993 | Mezrow et al. | 424/78.31 |
| 5,234,683 | 8/1993 | Hunter et al. | 424/78.31 |
| 5,234,908 | 8/1993 | Szabo et al. | 514/12 |
| 5,234,912 | 8/1993 | Marra et al. | 514/21 |

FOREIGN PATENT DOCUMENTS

| | | |
|---|---|---|
| 88/06038 | 8/1988 | WIPO. |
| WO89/01486 | 2/1989 | WIPO. |
| 92/16484 | 10/1992 | WIPO. |
| 92/19250 | 11/1992 | WIPO. |

OTHER PUBLICATIONS

Wang et al., Jour. of Parenteral Sci. & Tech, vol. 42, No. 2S, pp. S1–S26, 1988.

FDA, Division of Drug Information Resources, "Inactive Ingredient Guide" including list of Currently Marketed Injectable Products, (1991).

FDA review and basis for approval of OB–NDA–86–0909 on FLUOSOL® (20% Intravascular Perflorochemical Emulsion), The Green Cross Corp. (1989).

Genentech, Inc., "A Tissue Plasminogen Activator," Product Information (1987).

Gray et al., "Cloning of the cDNA of a Human Neutrophil Bactericidal Protein," *J. Biol. Chem.*, 264(16):9505–9509 (Jun. 5, 1989).

The Green Cross Corporation, "Perfluorochemical Blood Substitutes," Technical Info. Series Nos. 5 & 7 (1978 and 1981).

Henson et al., "The Surface Coagulation of Proteins During Shaking," *J. Colloid & Interface Sci.*, 32(1):162–165 (Jan. 1970).

ICI Americas, Inc., "ICI Americas Products For Cosmetics and Pharmaceuticals," Chapters 1–4, pp. 1–39 (1977).

ICI Americas, Inc., "The HLB System," Chapters 1–8, pp. 3–20 (1984).

Kaplan and Fraser, "Formation of Fibres from Protein Monolayers," *Nature*, 171(4352):559–560 (Mar. 28, 1953).

Krantz et al., "Sugar Alcohols," *Bulletin of School of Medicine, U. of MD*, 36:48–56 (1951).

Levine et al., "The Use of Surface Tension Measurements in the Design of Antibody–Based Product Formulations," *J. Parenteral Sci. & Tech.*, 45(3):160–165 (May–Jun. 1991).

MacRitchie, "Proteins at Interfaces," *Adv. Protein Chem.*, 32:283–326 (1978).

Neugebauer, "A Guide to the Properties and Uses of Detergents in Biology and Biochemistry," Calbiochem® Brand Chemicals, Hoechst Celanese Corp. (1987).

ORTHO Pharmaceutical Corporation, "Orthocolone OKT–3," Product Information Package Insert (1986).

The U.S. Pharmacopeia USPXXII, pp. 1763, 1857, and NFXVII, pp. 1960–1361, 1967–1968, 1990.

Wyandotte Chemicals Corporation, "Information on Applications of Pluronics," pp. 1–13 (Mar. 1, 1952).

*Primary Examiner*—Chhaya D. Sayala
*Attorney, Agent, or Firm*—Marshall, O'Toole, Gerstein, Murray & Borun

[57] ABSTRACT

Bactericidal/permeability increasing (BPI) polypeptide pharmaceutical compositions having improved stability and resistance to aggregation, particle formation and precipitation comprising the polypeptide pharmaceutical and poloxamer surfactants alone, or in combination with polysorbate suractants. Preferred BPI polypeptides stabilized are bactericidal/permeability increasing (BPI) protein, biologically active fragments of BPI, and biologically active analogs of BPI.

6 Claims, 10 Drawing Sheets

PHARMACEUTICAL COMPOSITION COMPRISING BPI PROTEINS

This is a continuation-in-part of U.S. patent application Ser. No. 08/012,360 filed Feb. 2, 1993 now abandoned.

BACKGROUND OF THE INVENTION

The present invention relates generally to pharmaceutical compositions and more specifically to improved protein and polypeptide pharmaceuticals for use as parenteral drugs. Recent advances in the development of genetic engineering technology have made a wide variety of biologically active polypeptides available in sufficiently large quantities for use as drugs. Polypeptides, however, can be subject to particulate formation and loss of biological activity by a variety of chemical and physical means including denaturation due to healing or freezing and by exposure to extreme pH or other chemical degradation.

Particulate formation and loss of biological activity can also occur as a result of physical agitation and interactions of polypeptide molecules in solution and at the liquid-air interfaces within storage vials. It is believed that the polypeptide molecules adsorb to an air-liquid interface, unfolding to present hydrophobic groups to air with the hydrophilic groups immersed in the aqueous phase. Once so positioned at the surface, the polypeptide molecules are susceptible to aggregation, particle formation and precipitation. It is also believed that further conformational changes can occur in polypeptides adsorbed to air-liquid and solid-liquid interfaces during compression-extension of the interfaces such as occurs from agitation during transportation or otherwise. Such agitation can cause the protein to entangle, aggregate, form particles and ultimately precipitate with other absorbed proteins.

Particle formation due to surface denaturation can be somewhat controlled by appropriate selection of the dimensions of storage vials and by minimizing the air volume (headspace) in those vials. In this regard, partially filled containers represent the worst case for vibration induced precipitation.

Particle formation can also be controlled by incorporation of surfactants into the protein containing composition in order to lower the surface tension at the solution-air interface. Classic stabilization of pharmaceuticals by surfactants or emulsifiers has focused on the amphipathic nature of molecular groups containing both hydrophilic and hydrophobic properties within the surfactant molecule. Thus, the art teaches that one can make a stable solution of immiscible molecules such as oil-in-water or water-in-oil by selecting an appropriate surfactant as a compatibilizer. One example is the stable emulsification of soybean oil using poloxamer 188 (PLURONIC F-68, BASF Wyandotte Corp., Parsippany, N.J.). Another example is the use of polysorbate 80 (TWEEN 80, ICI Americas, Inc., Wilmington, Del.) to emulsify oil-soluble vitamins A, E and K in aqueous solution for administration via oral and vascular routes. Work by Krantz, et al., "Sugar Alcohols-XXVIII. Toxicologic, Pharmacodynamic and Clinical Observations on TWEEN 80," Bull. of the School of Med., U. of MD., 36,48 (1951) laid the groundwork leading to the listing of polysorbate 80 as a drug ingredient for which USP/NF requirements have been established in U.S. Pharmacopeia XXII.

Of interest to the present invention is the work related to use of polysorbate 80 for stabilization of antibody-based product formulations as described in Levine, et al., J. Parenteral Sci. Technol., 45, 3, 160–165 (1991). This work disclosed that the amount of surfactant required for stabilization was in excess of the theoretical minimum required to reduce surface tension. The work further showed that the need for excess surfactant beyond the theoretical minimum could be attributed to (1) the concentration required to maintain an intact protective layer on a turbulent interface during random shaking; and (2) to surfactant loosely associated with protein and bound to container walls.

Regulatory requirements limit the types and specific identities of surfactants that can be incorporated into parenteral compositions for injection into the human body. Generally accepted surfactants having a history of use and listed in the U.S. Pharmacopoeia XXII include poloxamer and polysorbate polymers. However, either of these alone may provide less than complete stabilization for the pharmaceutical compositions when used at concentrations of 0.1% or lower. Elevated concentrations of surfactant may pose increased risk of toxic effects, earlier onset of hemolysis, and observed changes in neutrophils and platelets, both of which are involved in blood complement activation. The highest safe concentration for poloxamer 188 in approved parenteral solutions is 2.7% when it is used in limited doses as a blood substitute and is diluted as much as 10 fold in the bloodstream. Similarly, polysorbate 80, approved in parenteral solutions for over 20 years, is rarely used in concentrations greater than 0.1% in solution volumes of 100 mL or more. Krantz et al., supra, identifies the onset of hemolysis in the dog for a polysorbate concentration of 0.1% at 90 minutes. Neonatal deaths have been associated with the use of polysorbate 80 at concentrations of greater than 1%. Accordingly, there exists a need in the art for pharmaceutical compositions providing improved protein stability which comprise only those components which are regarded as safe and are included in parenterals approved by regulatory authorities for commercial use.

SUMMARY OF THE INVENTION

The present invention relates to pharmaceutical compositions of polypeptides and is directed to the discovery that poloxamer surfactants and combinations of poloxamer surfactants with polysorbate surfactants enhance the solubility/stability of bactericidal/permeability increasing (BPI) protein, biologically active fragments of BPI, biologically active analogs of BPI, and biologically active variants of BPI (produced by either recombinant or nonrecombinant means) in aqueous solution. The invention particularly provides for solubilization/stabilization of bactericidal/permeability increasing proteins which are biologically active amino-terminal fragments of BPI or analogs and variants thereof. Amino-terminal fragments of BPI, such as those designated rBPI$_{12}$ or any amino-terminal fragment comprising from about the first 193 to about the first 199 amino-terminal amino acid residues of BPI, are believed to be particularly susceptible to loss of stability in aqueous solution.

The present invention is directed in particular to the discovery that a combination of two specific types of surfactants provides a surprising improvement in protein stability to pharmaceutical compositions compared to either surfactant alone. Specifically, it has been found that a pharmaceutical composition comprising the combination of a poloxamer (polyoxypropylene-polyoxyethylene block copolymer) surfactant and polysorbate (polyoxyethylene sorbitan fatty acid ester) surfactant provides improved stability and resistance to aggregation, particle formation and precipitation of protein pharmaceutical agents. The combination of these two types of surfactants provides improved stability and resistance to surface denaturation, aggregation, particle formation and precipitation compared with either surfactant alone.

The poloxamer surfactant component is preferably present in a concentration of from about 0.01% to about 1% by weight with a concentration of 0.1% to 0.2% by weight being preferred to stabilize protein solutions comprising less than or equal to 2 mg/mL. The polysorbate surfactant component is preferably present in a concentration of from about 0.0005% to about 1% by weight with a concentration of 0.002% by weight being preferred. Most preferred is the combination comprising 0.1% to 0.2% by weight of poloxamer 188 and 0.002% by weight polysorbate 80. This combination is particularly useful for preventing particle formation of extremely degradation sensitive proteins such as bactericidal/permeability increasing protein (BPI) but is also useful for promoting the stability of other polypeptide pharmaceuticals. It is contemplated that the combination of poloxamer and polysorbate surfactants may be used alone or in combination with additional surfactants. Moreover, the invention is not limited to a single poloxamer surfactant in combination with a single polysorbate surfactant and can include one or more poloxamer surfactants in combination with one or more polysorbate surfactants.

A further aspect of the invention relates to the discovery that a poloxamer surfactant is particularly useful for the solubilization/stabilization of compositions comprising an aqueous solution of BPI protein or biologically active fragments, analogs, or variants of BPI protein (produced by recombinant or nonrecombinant means). The invention provides a method of solubilizing/ stabilizing such polypeptides by contacting the polypeptide with a poloxamer surfactant. Without being bound by a theory of the invention, it is believed that poloxamer surfactants stabilize BPI protein products not by a mechanism involving lowering the surface tension of the aqueous solution, but, at elevated temperatures, by stabilizing unfolded and partially unfolded BPI protein molecules and preventing precipitation of those molecules.

Preferred poloxamer surfactants are characterized by a HLB value greater than about 14 and a surface tension between 10 and 70 mN/m as measured in aqueous solution at room temperature and at a concentration of 0.1%. More preferred is a poloxamer surfactant which has an HLB value between about 25 and 35 and has a surface tension between 30 and 52 mN/m as measured in aqueous solution at room temperature and at a concentration of 0.1%. Most preferred is poloxamer 188 available commercially as PLURONIC F-68 (BASF Wyandotte, Parsippany, N.J.) which is characterized by a surface tension of 50 mN/m and by an HLB value of 29.

A preferred polysorbate surfactant preferably has a surface tension between 10 and 70 mN/m as measured in aqueous solution at room temperature and at a concentration of 0.1%. More preferably, the polysorbate surfactant is characterized by a hydrophilic/lipophilic balance (HLB) value of about 15 and by a surface tension between 40 and 50 mN/m as measured in aqueous solution at room temperature and at a concentration of 0.1%. Most preferred is polysorbate 80 (sorbitan mono-9-octadeconoate) which is available commercially as TWEEN 80 (ICI Americas Inc., Wilmington, Del.).

DETAILED DESCRIPTION

Figure 1:
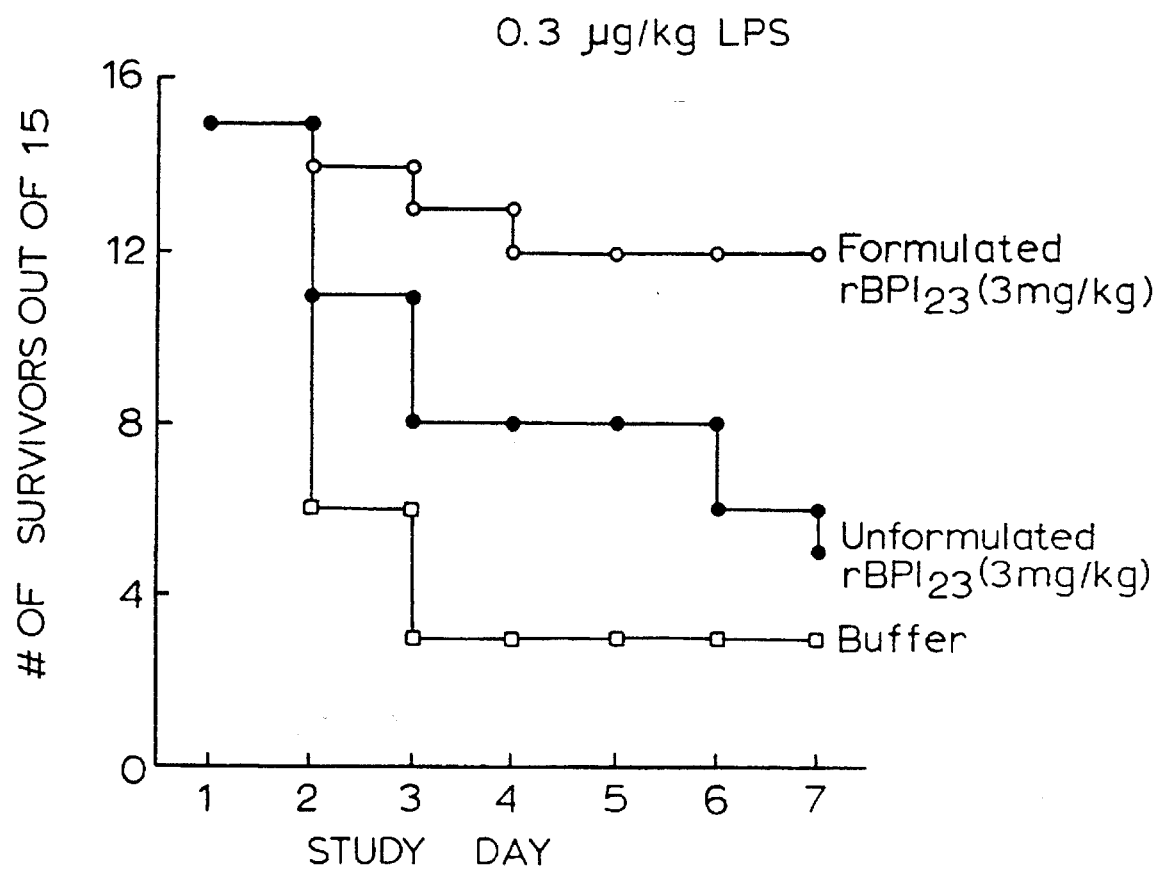
FIG. 1 is a graph depicting survival results over time of an actinomycin-D sensitized mouse model.

The present invention provides improved methods and materials for maintaining the stability of polypeptide pharmaceuticals and preventing surface denaturation of such biologically active polypeptides. Specifically, the invention relates to the discovery that a combination of two specific types of surfactant molecules provides synergistic improvements in stabilization from surface denaturation of polypeptide pharmaceuticals. The invention also relates to the discovery that poloxamer surfactants have unique properties in the solubilization/stabilization of BPI-related proteins. While specific embodiments of the invention are directed to stabilization of bactericidal/permeability increasing protein (BPI) and biologically active fragments and/or analogs or variants thereof which are particularly susceptible to denaturation and particle formation, the utility of the invention extends generally to all protein and polypeptide pharmaceuticals. BPI and active fragments and analogs thereof useful with the present invention include recombinant produced proteins such as described in U.S. Pat. No. 5,198,541. Co-owned, copending patent application Theofan et al., U.S. Ser. No. 08/064,693 filed May 19, 1993, which is a continuation-in-part application of U.S. Ser. No. 07/885,911 filed May 19, 1992, now abandoned, addresses BPI-Immunoglobulin fusion proteins which are variants of BPI protein comprising at the amino terminal a BPI protein or a biologically active fragment thereof, and retaining the same biological activity of BPI protein. Particularly preferred BPI materials include recombinant produced polypeptides produced according to the method of co-owned and copending Theofan et al. U.S. application Ser. No. 08/013,801 filed Feb. 2, 1993 and entitled "Stable Bactericidal/Permeability-Increasing Protein Products and Pharmaceutical Compositions Containing the Same," the disclosure of which is herein incorporated by reference. A preferred BPI fragment is characterized by about 1 to 199 or about 1 to 193 of the amino-terminal amino acid residues of the mature human BPI molecule as set out in Gray et al., J. Biol. Chem., 264, 9505–9509 (1989) except that residue 185 is glutamic acid rather than lysine as specified in Gray. The recombinant expression product of DNA encoding BPI amino acids 1 to 199 has been designated $rBPI_{23}$. The recombinant expression product of DNA encoding BPI amino acids 1 to 193 has been designated rBPI(1–193). A preferred BPI fragment analog comprises the first 193 amino acid residues as set out in Gray except that residue 185 is glutamic acid rather than lysine and the cysteine at position 132 is replaced with a non-cysteine residue such as alanine. Such a protein is designated $rBPI_{21}\Delta cys$ or $rBPI(1-193)ala^{132}$. Another BPI fragment analog comprises the first 199 amino acid residues as set out in Gray except that residue 185 is glutamic acid rather than lysine and the cysteine at position 132 is replaced with a non-cysteine residue such as alanine. Such a protein is designated $rBPI(1-199)ala^{132}$, as referred to in Example 4.

EXAMPLE 1

In this example, tests of various surfactant systems were conducted to determine their utility for surface stabilization of a polypeptide pharmaceutical ($rBPI_{23}$). The $rBPI_{23}$ was provided at a concentration of 1 mg/mL in citrate buffered saline (0.02M citrate, 0.15M NaCl pH 5.0). Various surfactants were then added to this preparation in order to determine their utility as stabilizers.

V) and fixed to the shaker by tape. Vials were then shaken at 150 rpm at room temperature. At 0 hours, 2–4 hours, and 18 hours, 150 µl samples were withdrawn in a biosafety cabinet using a 1 mL syringe fitted with a 21 gauge needle. The starting, in process, and ending soluble $rBPI_{23}$ concentrations were determined by an ion exchange HPLC assay and visual observation of cloudiness of the solution was also recorded. The results are shown below in Table 1 in which acceptable stability was determined by visual inspection after the shake test.

Testing of protein preparations comprising single surfactants showed good results for use of octoxynol-9 (TRITON X-100, Rohm & Haas), laureth-4, (BRIJ 30, ICI Americas), poloxamer 403 (PLURONIC P123, BASF Wyandotte) and telomere B monoether with polyethylene glycol (ZONYL FSO-100, E.I. DuPont de Nemours). While these surfactants are capable of reducing surface tensions to low levels, they are not included in approved parenteral pharmaceuticals due to suspected toxic effects or unknown biocompatibility.

Testing of other surfactants as shown in Table 1 shows that surfactants producing a surface tension lower than 35 mN/m are capable of stabilizing rBPI at surfactant concentrations of 0.1%. This example further shows that both polysorbate 80 (TWEEN 80) and poloxamer 188 (PLURONIC F-68) were incapable of stabilizing the protein preparation alone under the shake test conditions employed. The incorporation of polysorbate 80 did, however, have the effect of clarifying a cloudy solution of BRIJ 30 which is not readily water soluble without the help of an additional solubilizer.

TABLE 1

| Exp No. | Surfactant Used | Surface Tension mN/m at 0.1% Conc. at Room Temp. in Water (w), Buffer (b)[1] | Surfactant Concentration in Form. Buffer | Visual Observation 3–4 hr | Visual Observation 18 hr | $rBPI_{23}$ Conc. by HPLC (mg/mL) 0 hr | $rBPI_{23}$ Conc. by HPLC (mg/mL) 3–4 hr | $rBPI_{23}$ Conc. by HPLC (mg/mL) 18 hr | Stability as Determined by Visual Inspection |
|---|---|---|---|---|---|---|---|---|---|
| 1 | ZONYL FSO-100 | 17$^{(w)}$ | 0.100% | — | Clear | 0.96 | — | 1.00 | Stable |
| 2 | PS-80 | 41$^{(b)}$ | 0.100% | — | Cloudy | 1.11 | — | 0.02 | Unstable |
| 3 | BRIJ 30 | 27.5$^{(b)}$ | 0.500% | Cloudy | Cloudy | 1.08 | — | 1.14 | BRIJ 30 alone is cloudy. |
| 4 | TRITON X-100 | 32$^{(b)}$ | 0.100% | Clear | Clear | 1.00 | 1.01 | 0.98 | Stable |
| 5 | PLUR P123 | 34.3$^{(w)}$ | 0.100% | Clear | Clear | 1.08 | 1.08 | 1.08 | Stable |
| 6 | BRIJ 30/PS-80 | — | 0.1%/0.125% | Clear | Clear | 1.19 | 1.21 | 1.17 | Stable |
| 7 | PLUR F-68 | 46$^{(b)}$ | 0.100% | Clear | Haze | 1.23 | 1.22 | 0.95 | Marginal stability. Slight haze, specks. |
| 8 | PLUR F-68 | 44$^{(b)}$ | 0.200% | Clear | Haze | — | — | 1.04 | Marginal Stability. Slight haze with a few specks. |
| 9 | PLUR F-68/PS-80 | 47$^{(b)}$ | 0.1%/0.001% | Clear | Clear | 1.14 | | 1.09 | Stable. Crystal clear with a few specks. |

Surface tensions with superscript w are obtained from the surfactant manufacturer. Surface tensions with superscript b are obtained experimentally using Wilhelmy plate method.

According to this test, $rBPI_{23}$ [BR-1] characterized by about 1 to about 199 of the first 199 amino acids of the mature human BPI molecule and produced according to the methods of Theofan et al., U.S. Pat. application Ser. No. 08/013,801 filed Feb. 2, 1993 was filled by hand to 5 mL in sealed sterile 6 mL molded glass vials (total capacity 8.4 mL, Wheaton) in the desired formulation buffer. The vials to be tested were set horizontally on a flat bed shaker (S/P rotor

EXAMPLE 2

In this example, additional comparisons were carried out according to the methods of Example 1 using various surfactants alone and in combination to stabilize a $rBPI_{23}$ preparation. The results are shown below in Table 2 in which acceptable stability was determined by visual inspection after the shake test. The results, particularly those of experiments 52–58 show the unexpected utility of the combination of poloxamer 188 and polysorbate 80 for stabilizing the rBPI$_{23}$ composition at concentrations where either surfactant alone is incapable of equivalently stabilizing the material under the conditions of the test. The experiments show that various combinations of concentrations of the two surfactants exhibit synergistic effects but that the preferred combination specific to rBPI$_{23}$ at 1 mg/mL concentration is that having 0.1% by weight poloxamer 188 and 0.001% by weight polysorbate 80 in citrate buffered saline (0.02M citrate, 0.15 NaCl, pH 5.0). The results with polysorbate 80 at concentrations lower than 0.001% produced prompt cloudiness after 18 hours of shaking, but with only a small loss of protein as determined by ion-exchange HPLC MA7C column (Bio-Rad, Hercules, Calif.). Nevertheless, the cloudiness is unacceptable for appearance and suggests lowered stability. Testing with polysorbate 80 at concentrations of 0.005% and above all give good stability at up to 18 hours of shaking with little sign of protein loss by HPLC. Nevertheless, these higher concentrations of polysorbate 80 may provide less stability during long-term storage at 4° C. and at stress temperatures of ambient room temperature or above.

TABLE 2

| Exp No. | Surfactant Used | Surfactant Conc. in Form. Buffer | Visual Observation 3–4 hr | Visual Observation 18 hr | Conc. by HPLC (mg/mL) 0 hr | Conc. by HPLC (mg/mL) 3–4 hr | Conc. by HPLC (mg/mL) 18 hr | Stability as Determined by Visual Inspection |
|---|---|---|---|---|---|---|---|---|
| 1 | ZONYL FSO-100 | 0.100% | — | Clear | 0.96 | — | 1.00 | Stable |
| 2 | PS-80 | 0.100% | — | Cloudy | 1.11 | — | 0.02 | Unstable |
| 3 | Dextran Sulfate | 1 mg/mL | — | Cloudy | — | — | 0.00 | Unstable |
| 4 | Glycerol | 10.0% | — | Cloudy | 0.86 | — | 0.02 | Unstable |
| 5 | HSA | 5.0% | — | Cloudy | 0.92 | — | 0.00 | Unstable |
| 6 | Control- 5 mL Fill Volume | — | — | Cloudy | 1.13 | — | 0.03 | Unstable |
| 7 | Control 8.4 mL (complete) Fill Volume | — | — | Clear | 1.13 | — | 1.04 | Stable. One speck of precipitate. |
| 8 | Control- 5 mL (partial) Fill Volume | — | Cloudy | Cloudy | 1.16 | 0.21 | 0.00 | Unstable |
| 9 | TRITON X-100 | 0.500% | Clear | Clear | 1.04 | 0.99 | 1.11 | Stable |
| 10 | PS-80 | 0.500% | Clear | Cloudy | 1.12 | 0.95 | 0.59 | Unstable |
| 11 | PLURONIC P123 | 0.500% | Clear | Clear | 1.15 | — | 1.13 | Stable |
| 12 | BRIJ 30 | 0.500% | Cloudy | Cloudy | 1.08 | — | 1.14 | BRIJ 30 alone is cloudy. |
| 13 | TRITON X-100 | 0.100% | Clear | Clear | 1.00 | 1.01 | 0.98 | Stable |
| 14 | TRITON X-100 | 0.010% | Slt. Haze | Cloudy | 0.96 | 0.84 | 0.04 | Unstable |
| 15 | PLURONIC P123 | 0.100% | Clear | Clear | 1.08 | 1.08 | 1.08 | Stable |
| 16 | PLURONIC P123 | 0.100% | Clear | Clear | 1.23 | 1.26 | 0.94 | Stable |
| 17 | PLURONIC P123 | 0.050% | Clear | Slt. Haze | 1.21 | 1.18 | 1.11 | Unstable |
| 18 | PLURONIC P123 | 0.010% | Cloudy | Cloudy | 1.14 | 0.00 | 0.00 | Unstable |
| 19 | BRIJ 30/ PS-80 | 0.1%/ 0.125% | Clear | Clear | 1.19 | 1.21 | 1.17 | Stable |
| 20 | BRIJ 30/ PS-80 | 0.075%/ 0.094% | Clear | Clear | 1.22 | 1.20 | 1.18 | Stable |
| 21 | BRIJ 30/ PS-80 | 0.03%/ 0.038% | Slt. Haze | Cloudy | 1.20 | 1.05 | 0.41 | Unstable |
| 22 | BRIJ 30/ PS-80 | 0.01%/ 0.013% | Cloudy | Cloudy | 1.14 | 0.48 | 0.00 | Unstable |
| 23 | PLURONIC F68 | 0.100% | Clear | Slt. Haze | 1.23 | 1.22 | 0.95 | Marginal Stability |
| 24 | PLURONIC F68 | 0.100% | Clear | Slt. Haze | — | — | 1.00 | Marginal Stability |
| 25 | PLURONIC F68 | 0.150% | Clear | Slt. Haze | — | — | 1.06 | Marginal Stability |
| 26 | PLURONIC F68 | 0.200% | Clear | Slt. Haze | — | — | 1.04 | Marginal Stability |
| 27 | PLURONIC F68 | 0.300% | Clear | Slt. Haze | — | — | 1.10 | Marginal Stability |
| 28 | PLURONIC F68 | 0.500% | Clear | Slt. Haze | — | — | 1.08 | Marginal Stability |
| 29 | PLURONIC P123 | 0.070% | Clear | Clear | 1.06 | 1.08 | 0.97 | Marginal Stability |
| 30 | BRIJ 30/ | 0.05%/ | Clear | Clear | 1.04 | 1.01 | 1.01 | Stable |

TABLE 2-continued

| Exp No. | Surfactant Used | Surfactant Conc. in Form. Buffer | Visual Observation 3-4 hr | 18 hr | Conc. by HPLC (mg/mL) 0 hr | 3-4 hr | 18 hr | Stability as Determined by Visual Inspection |
|---|---|---|---|---|---|---|---|---|
| 31 | PLUR F68/ PS-80 | 0.063% 0.1%/ 0.1% | Clear | Clear | 1.05 | 1.06 | 1.10 | Stable |
| 32 | PLUR F68/ BRIJ 30 | 0.1%/ 0.03% | Clear | Clear | 1.05 | 1.05 | 1.03 | Stable |
| 33 | PLUR F68/ BRIJ 30 | 0.1%/ 0.01% | Clear | Clear | 1.06 | 1.04 | 1.05 | Stable |
| 34 | PLURONIC F88 | 0.100% | Cloudy | Cloudy | 1.07 | 0.87 | 0.56 | Unstable |
| 35 | PLURONIC F98 | 0.100% | Cloudy | Cloudy | 1.04 | 0.77 | 0.39 | Unstable |
| 36 | PLURONIC F108 | 0.100% | Clear | Cloudy | 1.04 | 0.87 | 0.55 | Unstable |
| 37 | PLURONIC F127 | 0.100% | Clear | Clear | 1.06 | 1.04 | 0.98 | Marginal Stability |
| 38 | PLUR F68/ BRIJ 30 | 0.075%/ 0.01% | Clear | Clear | 1.12 | — | 1.11 | Stable |
| 39 | PLUR F68/ BRIJ 30 | 0.05%/ 0.01% | Clear | Clear | 1.12 | — | 1.09 | Stable |
| 40 | PLUR F68/ BRIJ 30 | 0.025%/ 0.01% | Clear | Clear | 1.10 | — | 1.04 | Stable |
| 41 | PLUR F68/ BRIJ 30 | 0.01%/ 0.01% | Cloudy | Cloudy | 1.07 | — | 0.64 | Unstable |
| 42 | PLURONIC F127 | 0.100% | Clear | Clear | 1.12 | — | 0.93 | Marginal Stability |
| 43 | PLURONIC F127 | 0.075% | Clear | Clear | 1.10 | — | 0.61 | Unstable |
| 44 | PLURONIC F127 | 0.050% | Clear | Slt. Haze | 1.09 | — | 0.20 | Unstable |
| 45 | PLURONIC F127 | 0.025% | Slt. Haze | Cloudy | 1.07 | — | 0.00 | Unstable |
| 46 | PLURONIC F127 | 0.010% | Cloudy | Cloudy | 1.06 | — | 0.00 | Unstable |
| 47 | PLUR F68/ BRIJ 30 | 0.05%/ 0.01% | Clear | Clear | 1.04 | — | 1.01 | Stable |
| 48 | PLUR F68/ BRIJ 30 | 0.05%/ 0.008% | Clear | Clear | 1.01 | — | 1.01 | Stable |
| 49 | PLUR F68/ BRIJ 30 | 0.05%/ 0.005% | Clear | Clear | 1.00 | — | 1.03 | Stable |
| 50 | PLUR F68/ BRIJ 30 | 0.03%/ 0.008% | Clear | Clear | 1.06 | — | 0.99 | Marginal Stability |
| 51 | PLUR F68/ BRIJ 30 | 0.03%/ 0.005% | Clear | Cloudy | 1.01 | — | 0.79 | Unstable |
| 52 | PLUR F68/ PS-80 | 0.1%/ 0.05% | Clear | Clear | 1.14 | — | 1.11 | Stable. A few specks. |
| 53 | PLUR F68/ PS-80 | 0.1%/ 0.01% | Clear | Clear | 1.14 | — | 1.11 | Stable. A few specks. |
| 54 | PLUR F68/ PS-80 | 0.1%/ 0.005% | Clear | Clear | 1.15 | — | 1.10 | Stable. A few specks. |
| 55 | PLUR F68/ PS-80 | 0.1%/ 0.001% | Clear | Clear | 1.14 | — | 1.09 | Stable. A few specks. |
| 56 | PLUR F68/ PS-80 | 0.1%/ 0.0005% | Clear | Cloudy | 1.12 | 1.09 | 1.02 | Unstable |
| 57 | PLUR F68/ PS-80 | 0.1%/ 0.0001% | Slt. Haze | Cloudy | 1.09 | 1.09 | 1.02 | Unstable |
| 58 | PLUR F68/ PS-80 | 0.05%/ 0.001% | Clear | Cloudy | 1.08 | 1.00 | 0.72 | Unstable |

EXAMPLE 3

In this example, a study was conducted to compare the efficacy of rBPI$_{23}$ formulated with and without the preferred formulation of the invention in an actinomycin-D sensitized mouse model according to Pieroni et al., Proc. Soc. Exp. Biol. & Med.; 133,790 (1970). According to this example, ICR mice were administered an intravenous injection of actinomycin-D (800 μg/kg). Immediately thereafter, groups of 15 mice each received an injection of one of several doses of rBPI$_{23}$ [BR-1] characterized by about 1 to about 199 of the first 199 amino acids of the mature human BPI molecule and produced according to the methods of Theofan et al., U.S. patent application Ser. No. 08/013,801 filed Feb. 2, 1993 at 1 mg/mL in citrate buffered saline (0.2M citrate, 0.15M NaCl, pH 5.0). The mouse injections were at dosages of 0.03, 0.1, 1.0 and 3.0 mg/kg. As a control, some animals received the formulation buffer with or without the poloxamer and polysorbate surfactants. Deaths were recorded over seven days.

Figure 2:
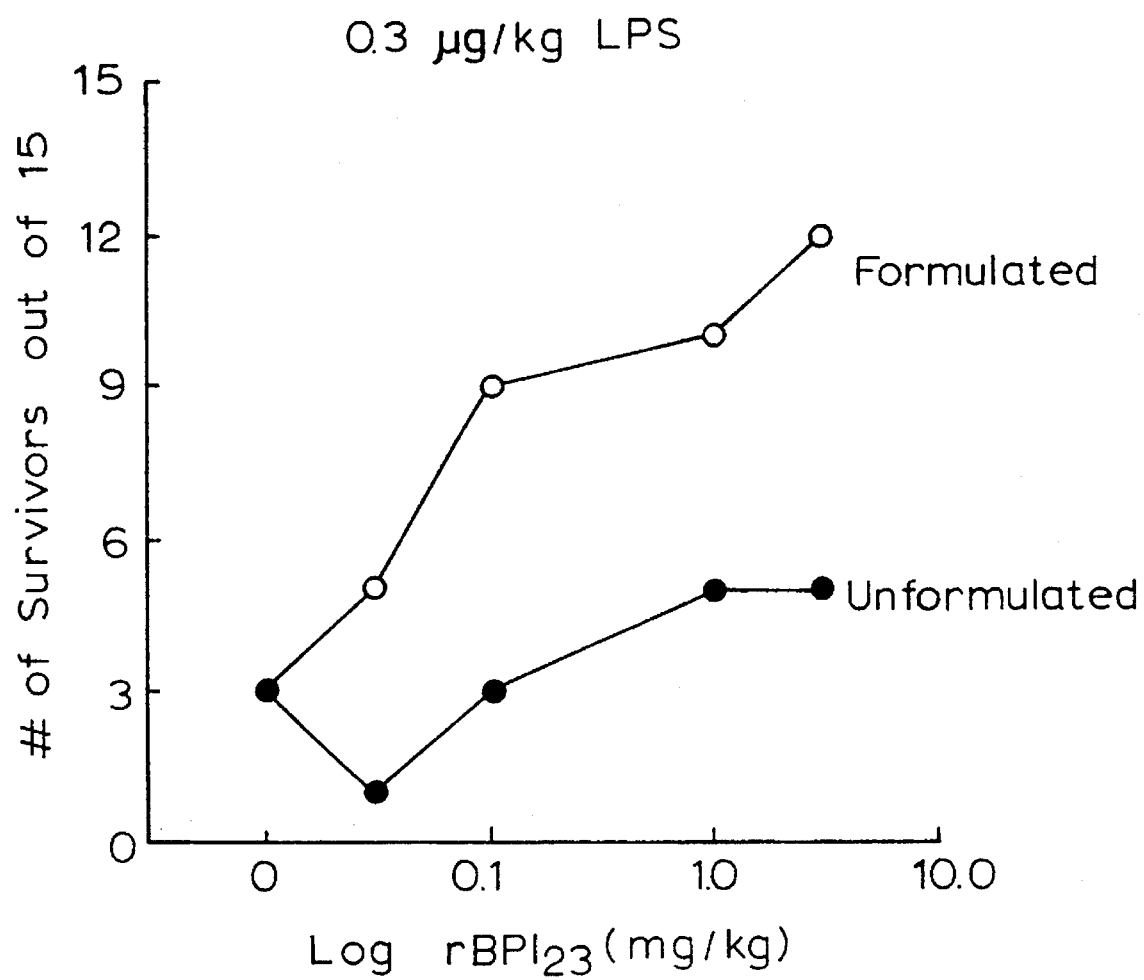
FIG. 2 is a graph depicting survival results according to BPI dose in an actinomycin-D mouse model.

The results are shown in FIGS. 1 and 2. FIG. 1 shows the number of mice surviving on each study day in the buffer and 3.0 mg/kg rBPI$_{23}$ treatment groups. For both buffer groups (with or without poloxamer and polysorbate surfactants), mortality was 80% overall. In contrast, rBPI$_{23}$ in the presence of excipients was even more potent than either buffer or rBPI$_{23}$ without excipients. FIG. 2 summarizes the data for the different dose groups at day 7 (final survivors). Beginning at the 0.1 mg/kg dose level, rBPI$_{23}$ formulated with the preferred surfactant formulations provided significantly greater protection to the lethal effects of LPS ($P<0.05$ or better) than did rBPI$_{23}$ in the absence of added excipients.

EXAMPLE 4

In this example, experiments were conducted to determine the turbidity of various rBPI-containing pharmaceutical compositions with and without the preferred surfactant formulation of the invention. In this context, turbidity refers to the tendency of pharmaceutical compositions to engage in unfolding (i.e., loss of tertiary protein structure) and/or particle formation (interactions between individual proteins to form larger (>10 μm) particles). The pharmaceutical compositions tested contained either rBPI(1–199)ala$^{132}$, rBPI(1–193)ala$^{132}$ or various samples of rBPI$_{23}$ produced according to co-owned and co-pending U.S. patent application Ser. No. 08/013,801 filed Feb. 2, 1993 in either a citrate buffer (20 mM sodium citrate/150 mM sodium chloride, pH 5.0) or a citrate buffer containing 0.1% ipoloxamer 188 and 0.002% polysorbate 80.

Samples were analyzed to determine their resistance to turbidity over time at increasing temperature and at pH 7.0. Prior to analysis, all samples were diluted to a concentration of 0.1 mg/mL in 50 mM potassium phosphate at pH 7.0. Turbidity measurements were obtained by placing samples in quartz cuvettes for use in a Shadzu UV-160 UV-Vis spectrophotometer equipped with a temperature-controlled cuvette holder attached to a recirculating water bath. Upon equilibrating the cuvette holder at 57° C., absorbance at 280 nm was measured to confirm that samples had been diluted to the proper concentration. Following this, the absorbance of samples at 350 nm was measured every 2 minutes for 1 hour to determine the change in absorbance over time.

Figure 3:
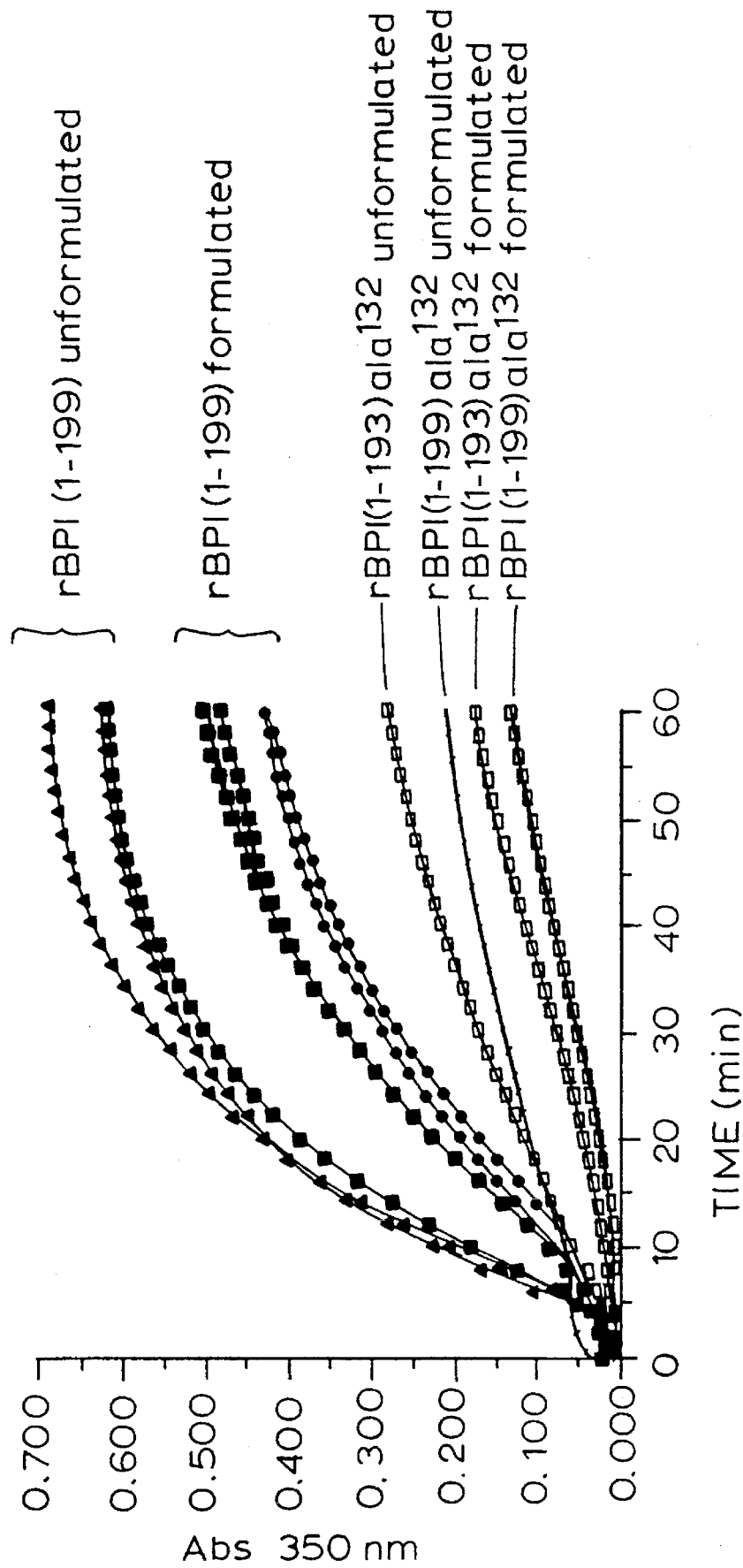
FIG. 3 is a graph depicting turbidity measurements of various BPI proteins with and without the preferred surfactants of the invention.

Results are presented in FIG. 3 showing a lower rate of change in turbidity (i.e. a lower rate of increase in absorbance over time), indicating increased stability against the formation of particles. As shown in FIG. 3, the addition of the preferred combination of surfactants resulted in increased stability (resistance to particle formation) of all compositions tested. Moreover, the rBPI(1–199)ala$^{132}$ and rBPI(1–193)ala$^{132}$ exhibited greatly improved resistance to particle formation relative to wild-type compositions [rBPI$_{23}$].

EXAMPLE 5

In this example surface tension measurements were made of polysorbate and poloxamer surfactants or combinations of the two in solutions of the BPI protein product rBPI$_{21}$Δcys according to the procedure set out in the Krüss Digital Tensiometer K10ST Users Manual, Chapter 4: Measuring with the Plate. A decrease in surface tension indicates an increase in the surface activity of the surfactant, which has conventionally been thought to be the mechanism by which surfactants stabilize proteins. These procedures established that poloxamer surfactants provide advantageous results by a different and unexpected mechanism.

Specifically, a 2 mg/mL solution of unformulated rBPI$_{21}$Δcys (lot 30216) was diluted with 20 mM sodium citrate, 150 mM sodium chloride, pH 5.0 rendering a 1 mg/mL solution. 15 mL of this solution was placed into a 50 mL glass beaker containing a mini stir bar. Surfactants poloxamer 188, polysorbate 80, or combinations of both were added incrementally up to 0.10%. Before each surface tension measurement, the platinum plate was heated above the reducing zone (blue flame) of a gas burner until the plate just began to glow red. The platinum plate was heated for about 10 to 15 seconds while turning the plate from side to side and then suspended back into the instrument. Each addition of surfactant was gently mixed using a magnetic stirrer and the solution was allowed to stand for 2 minutes on the thermostat vessel equilibrated at 4.6° C. The value for the surface tension was read after five minutes.

Figure 4:
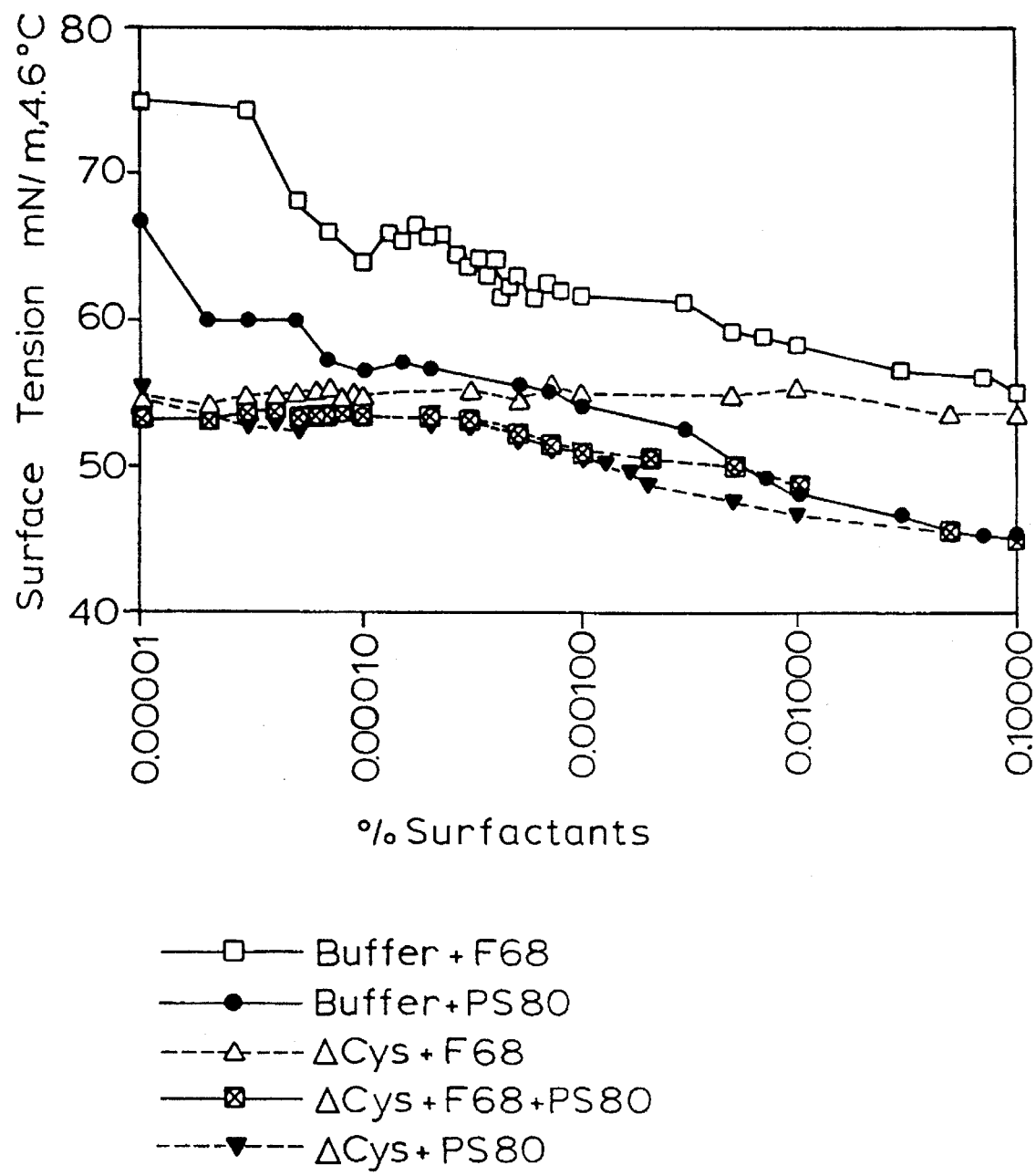
FIG. 4 is a graph depicting surface tension measurements of $rBPI_{21}\Delta cys$ solutions with varying surfactant concentrations of polysorbate 80 (PS80) and poloxamer 188 (F68).

The first part of this experiment evaluated the surface activity of the surfactants alone in buffer. Using the citrate saline buffer (20 mM sodium citrate, 150 mM sodium chloride, pH 5.0) as the baseline, surfactants were added incrementally. FIG. 4 is a plot of surface tension dependence on surfactant concentrations; the corresponding dam is presented in Table 3. The open squares represent the citrate saline buffer in varying concentrations of poloxamer 188 while the closed circles represent the same buffer in varying concentrations of polysorbate 80. The citrate-saline buffer solution alone had a surface tension of about 75 mN/m at 4.6° C., similar to H$_2$O. With increasing concentrations of surfactants, the buffer solution showed decreasing surface tension. With 0.10% poloxamer 188, the surface tension of the solution was 55 mN/m. On the other hand, with 0.10% polysorbate 80, the surface tension of the solution was 45 mN/m. The decrease in surface tension indicates an increase in the surface activity of the surfactant i.e., the lower the surface tension, the higher the surface activity. The results indicate that polysorbate 80 is more surface active than poloxamer 188.

In the second part of the experiment, the surface activity of rBPI$_{21}$ Δcys in the presence of surfactants was evaluated. The results show that rBPI$_{21}$ Δcys at 1 mg/mL in citrate saline buffer, pH 5.0, is surface active with a surface tension of about 54 mN/m at 4.6° C. The addition of polysorbate 80 (PS80) alone up to 0.0005% did not change the surface tension of rBPI$_{21}$ Δcys solution either (FIG. 4, closed triangles). At concentrations of polysorbate 80 exceeding 0.0005%, the surface tension of rBPI$_{21}$Δcys follows that of buffer with PS80 alone (no BPI), in which the surface tension of the solution decreases as the concentration of polysorbate 80 is gradually increased. For buffer with PS80 alone, the surface tension of 54 mN/m was reached when the PS80 concentration was increased from 0.0005%. These results indicate that when PS80 concentration is less than 0.0005%, the surface activity of the solution is dominated by rBPI$_{21}$Δcys. On the other hand, at PS80 concentration above 0.0005%, the surface activity of the solution is modulated by polysorbate 80. The addition of poloxamer 188 (F68) alone to rBPI$_{21}$Δcys up to 0.10% did not change the surface activity of rBPI$_{21}$Δcys solution significantly (FIG. 4, open triangles).

TABLE 3

| | 1 % F68 | 2 Buffer +F68 (mN/m) | 3 % PS80 | 4 Buffer +PS80 (mN/m) | 5 % F68 | 6 ΔCys +F68 (mN/m) | 7 % PS80 | 8 ΔCys +0.1% F68 +PS80 (mN/m) | 9 % PS80 | 10 ΔCys +PS80 (mN/m) |
|---|---|---|---|---|---|---|---|---|---|---|
| 1 | 0.00000 | 75.4 | 0.00000 | 75.1 | 0.00000 | 54.2 | 0.00000 | 53.7 | 0.00000 | 54.9 |
| 2 | 0.00001 | 74.9 | 0.00001 | 66.8 | 0.00001 | 54.7 | 0.00001 | 53.4 | 0.00001 | 55.0 |
| 3 | 0.00003 | 74.3 | 0.00002 | 60.0 | 0.00002 | 54.2 | 0.00002 | 53.3 | 0.00002 | 53.2 |
| 4 | 0.00005 | 68.2 | 0.00003 | 60.0 | 0.00003 | 54.9 | 0.00003 | 53.9 | 0.00003 | 53.3 |
| 5 | 0.00007 | 65.9 | 0.00005 | 60.0 | 0.00004 | 54.8 | 0.00004 | 53.9 | 0.00004 | 52.8 |
| 6 | 0.00010 | 64.0 | 0.00007 | 57.4 | 0.00005 | 55.0 | 0.00005 | 53.5 | 0.00005 | 52.4 |
| 7 | 0.00013 | 65.8 | 0.00010 | 56.6 | 0.00006 | 55.2 | 0.00006 | 53.5 | 0.00006 | 53.3 |
| 8 | 0.00015 | 65.4 | 0.00015 | 57.2 | 0.00007 | 55.4 | 0.00007 | 53.4 | 0.00007 | 53.6 |
| 9 | 0.00017 | 66.5 | 0.00020 | 56.7 | 0.00008 | 54.8 | 0.00008 | 53.8 | 0.00008 | 53.8 |
| 10 | 0.00020 | 65.7 | 0.00050 | 55.6 | 0.00009 | 55.0 | 0.00010 | 53.4 | 0.00009 | 53.2 |
| 11 | 0.00023 | 66.0 | 0.00070 | 55.3 | 0.00010 | 54.9 | 0.00020 | 53.5 | 0.00010 | 53.5 |
| 12 | 0.00027 | 64.4 | 0.00100 | 54.2 | 0.00030 | 55.3 | 0.00030 | 53.2 | 0.00020 | 53.2 |
| 13 | 0.00030 | 63.8 | 0.00300 | 52.7 | 0.00050 | 54.5 | 0.00050 | 52.3 | 0.00030 | 53.0 |
| 14 | 0.00033 | 64.1 | 0.00700 | 49.2 | 0.00070 | 55.5 | 0.00070 | 51.5 | 0.00050 | 52.0 |
| 15 | 0.00037 | 63.1 | 0.01000 | 48.3 | 0.00100 | 54.9 | 0.00100 | 51.0 | 0.00070 | 51.2 |
| 16 | 0.00040 | 64.2 | 0.03000 | 46.5 | 0.00500 | 54.9 | 0.00200 | 50.6 | 0.00100 | 50.5 |
| 17 | 0.00043 | 61.8 | 0.07000 | 45.3 | 0.01000 | 55.4 | 0.00500 | 50.1 | 0.00130 | 50.4 |
| 18 | 0.00047 | 62.4 | 0.10000 | 45.4 | 0.05000 | 53.6 | 0.01000 | 48.6 | 0.00170 | 49.8 |
| 19 | 0.00050 | 63.1 | | | 0.10000 | 53.7 | 0.05000 | 45.6 | 0.00200 | 48.8 |
| 20 | 0.00060 | 61.6 | | | | | 0.10000 | 45.0 | 0.00500 | 47.7 |
| 21 | 0.00070 | 62.5 | | | | | | | 0.01000 | 46.7 |
| 22 | 0.00080 | 62.0 | | | | | | | 0.05000 | 45.4 |
| 23 | 0.00100 | 61.7 | | | | | | | 0.10000 | 45.0 |
| 24 | 0.00300 | 61.2 | | | | | | | | |
| 25 | 0.00500 | 59.3 | | | | | | | | |
| 26 | 0.00700 | 58.9 | | | | | | | | |
| 27 | 0.01000 | 58.4 | | | | | | | | |
| 28 | 0.03000 | 56.6 | | | | | | | | |
| 29 | 0.07000 | 56.1 | | | | | | | | |
| 30 | 0.10000 | 55.1 | | | | | | | | |

EXAMPLE 6

Protein samples were analyzed by Differential Scanning Calorimetry (DSC) to study the unfolding (or denaturation) of the protein. The starting materials for DSC analysis were identical to those used in the surface tension measurement. A series of rBPI$_{21}$Δcys solutions was prepared with varying concentrations of surfactants, poloxamer 188, polysorbate 80 or combinations of both, and diluted with buffer (20 mM sodium citrate, 150 mM sodium chloride, pH5.0) to give a final rBPI$_{21}$Δcys concentration of 1 mg/mL. A series of buffer solutions was also prepared with surfactants at the same concentrations as in the rBPI$_{21}$Δcys solutions to serve as blanks for DSC. Each solution was filtered and placed into a 2 mL sterile plastic vial. The samples were packed into a 4° C. cold box until subjected to DSC Analysis.

The behavior of rBPI$_{21}$Δcys was evaluated as the temperature of the solution was gradually increased from ambient temperature to about 90° C., at a rate of 1° C. per minute. As the temperature is increased two events occur. The first event is an unfold reaction, which is endothermic, and is illustrated by an upward peak in the scans. The second event is precipitation, which is exothermic, and is depicted by a downward peak in the scans. In the scans depicted in FIGS. 5, 6 and 8–10, each scan is offset to facilitate analysis of data. In the rBPI$_{21}$Δcys solution not containing surfactants (FIG. 5, Scan 1) the unfolding of the protein at 65° C. was followed immediately by the second event, precipitation of the protein at 66° to 67° C.

Figure 5:
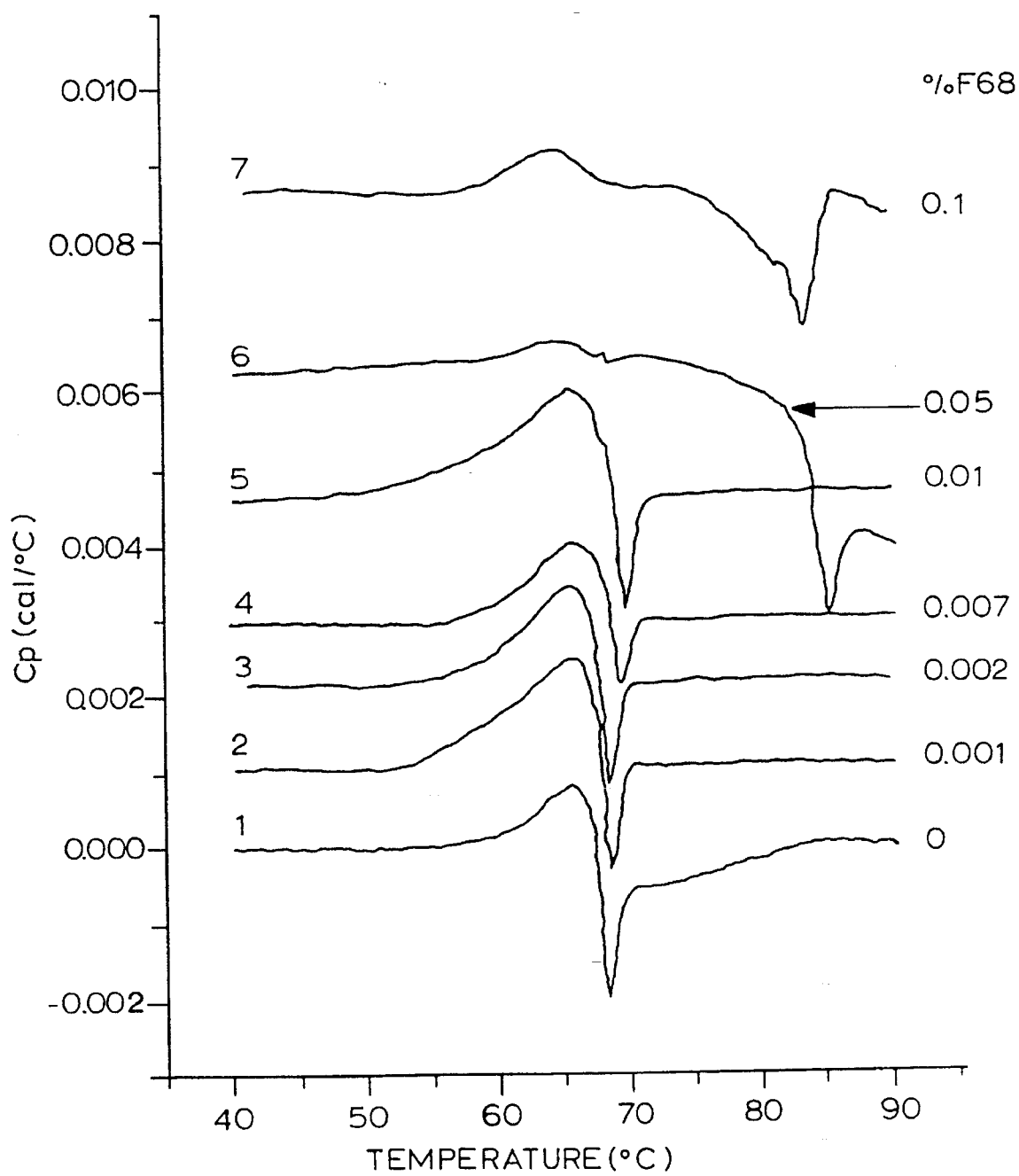
FIG. 5 is a series of graphs of differential scanning calorimetry results of $rBPI_{21}\Delta cys$ with various concentrations of the surfactant poloxamer 188 (F68).
Figure 6:
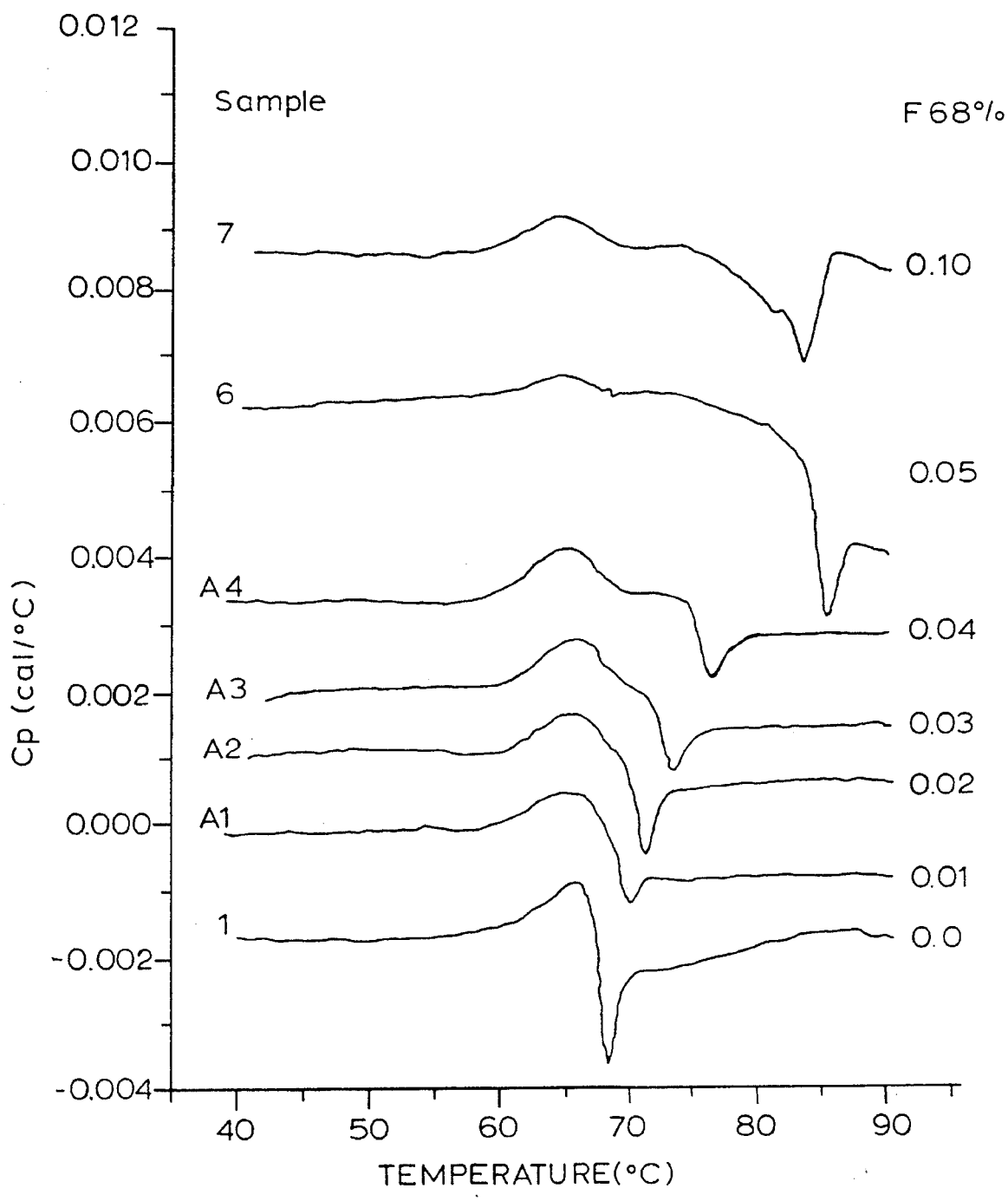
FIG. 6 is another series of graphs of differential scanning calorimetry results of $rBPI_{21}\Delta cys$ with various concentrations of poloxamer 188 (F68)
Figure 7:
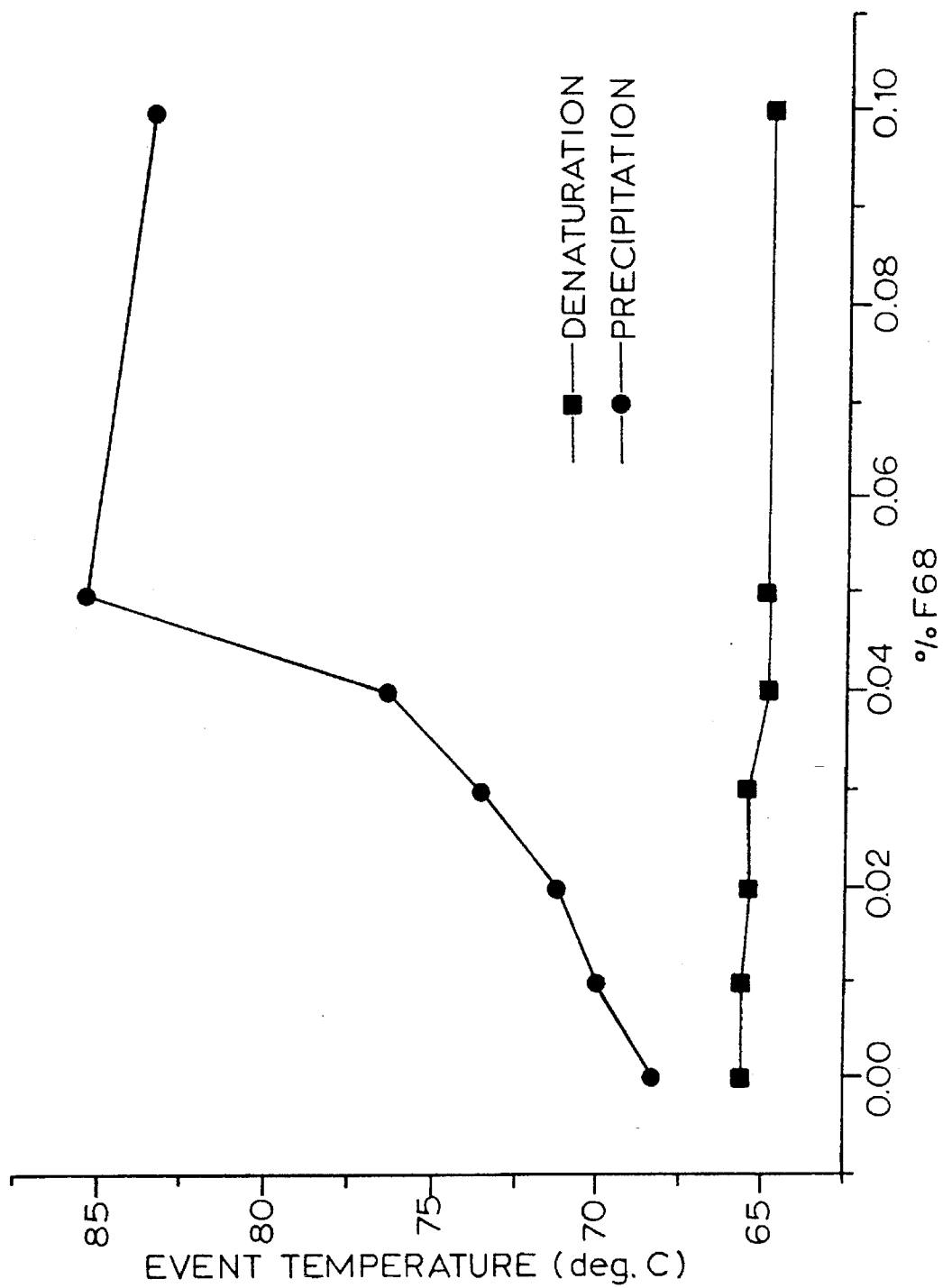
FIG. 7 is a plot of the denaturation and precipitation temperatures of $rBPI_{21}\Delta cys$ over varying concentrations of the surfactant poloxamer 188 (F68).
Figure 8:
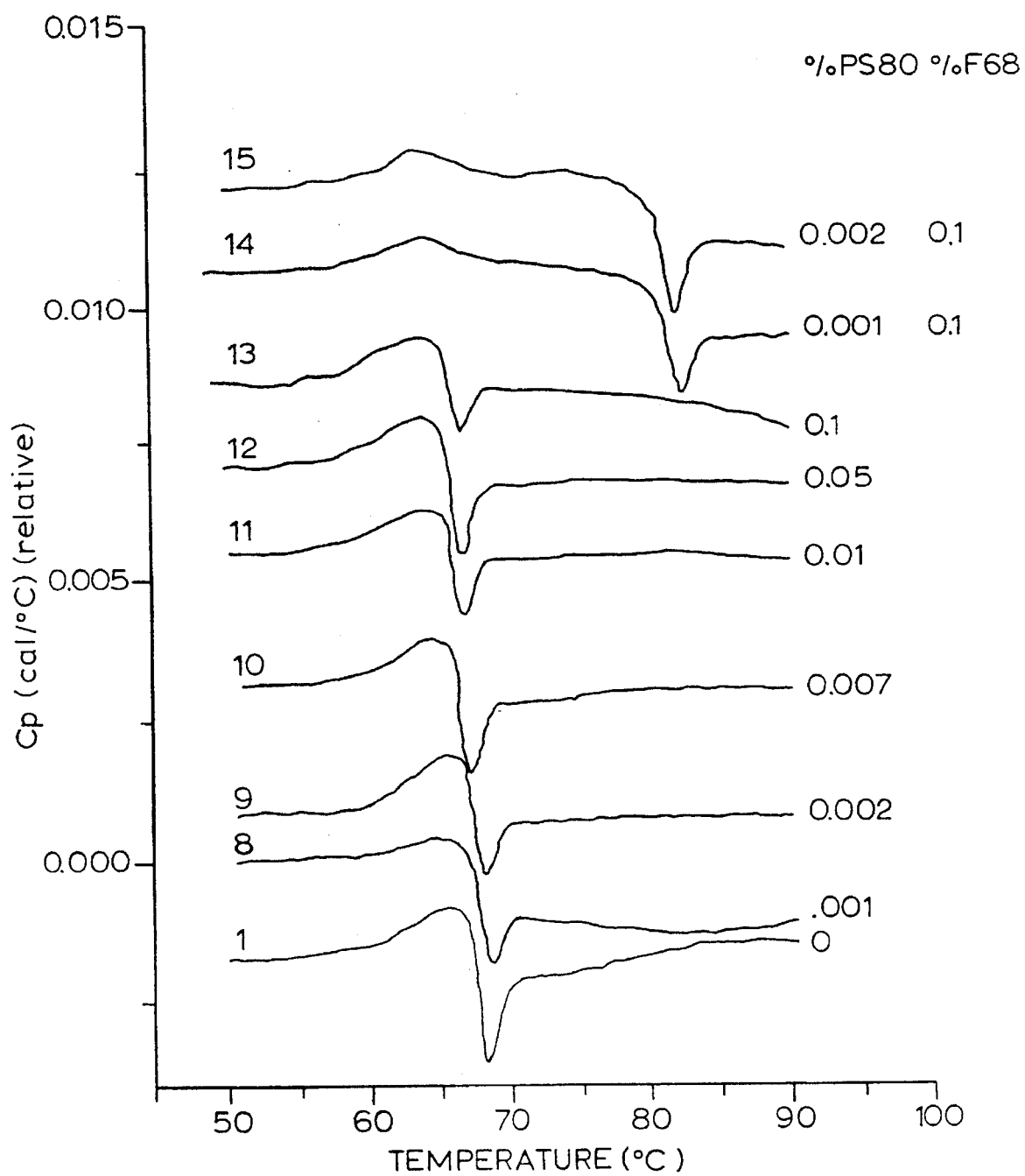
FIG. 8 is a series of graphs of differential scanning calorimetry results of $rBPI_{21}\Delta cys$ with various concentrations of polysorbate 80 (PS80) alone or in combination with 0.1% poloxamer 188 (F68) by weight.
Figure 9:
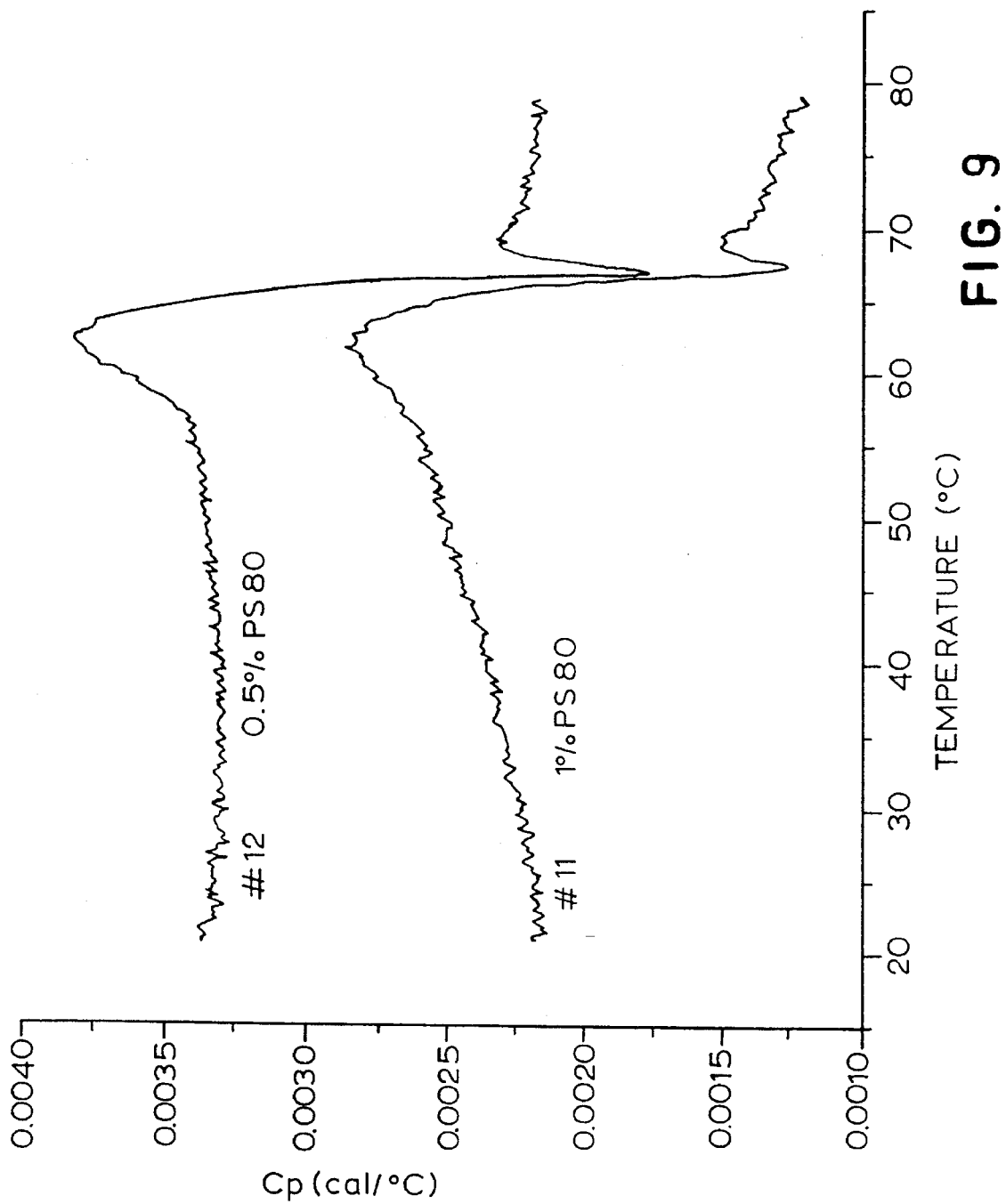
FIG. 9 is a set of graphs of differential scanning calorimetry results of $rBPI_{21}\Delta cys$ with the surfactant polysorbate 80 (PS80) at two different concentrations.

With low poloxamer 188 (PLURONIC® F68) concentrations ranging between 0.001% to 0.01%, the unfolding and precipitation events are similar to the rBPI$_{21}$Δcys solution without surfactants (FIG. 5, Scans 2 to 5), i.e. as rBPI$_{21}$Δcys unfolds, precipitation takes place immediately. With poloxamer 188 concentrations exceeding 0.05%, the unfolding of rBPI$_{21}$Δcys still occurs at 65° C., but precipitation does not occur until the temperature reaches 85° C. (FIG. 5, Scan 6). FIG. 6 shows that at poloxamer 188 concentrations between 0.01% and 0.05%, there is a gradual transition of delayed precipitation of unfolded BPI. These results suggest that at poloxamer 188 concentrations higher than 0.01%, unfolded rBPI$_{21}$Δcys be stabilized and the occurrence of precipitation is delayed. A plot of denaturation and precipitation temperature dependence over the surfactant (poloxamer 188) concentration is shown in FIG. 7. The effects of poloxamer 188 appear to delay the precipitation of rBPI$_{21}$Δcys to a higher temperature but not to stabilize its native structure as the $T_m$ (denaturation temperature) and $\Delta H$ (energy of denaturation) did not change.

rBPI$_{21}$Δcys formulated with polysorbate 80 at concentrations up to 1% was likewise analyzed. The isotherms were similar to rBPI$_{21}$Δcys solution without surfactants (FIG 8: Scans 1 and 8–13, FIG. 9: Scans 11, 12). Polysorbate 80 did not maintain the rBPI$_{21}$Δcys in solution at higher temperatures. The stabilization of unfolded rBPI$_{21}$Δcys is thus unique to poloxamer 188.

The two formulations using combined poloxamer 188 and polysorbate 80, namely 0.1%F68/0.001%PS80 and 0.1%F68/0.002%PS80, showed the same scan profile as rBPI$_{21}$Δcys containing 0.05% and 0.1% PLURONIC F68, with unfolding at 65° C. and precipitation at 85° C. (FIG. 8: Scans 14, 15).

Figure 10:
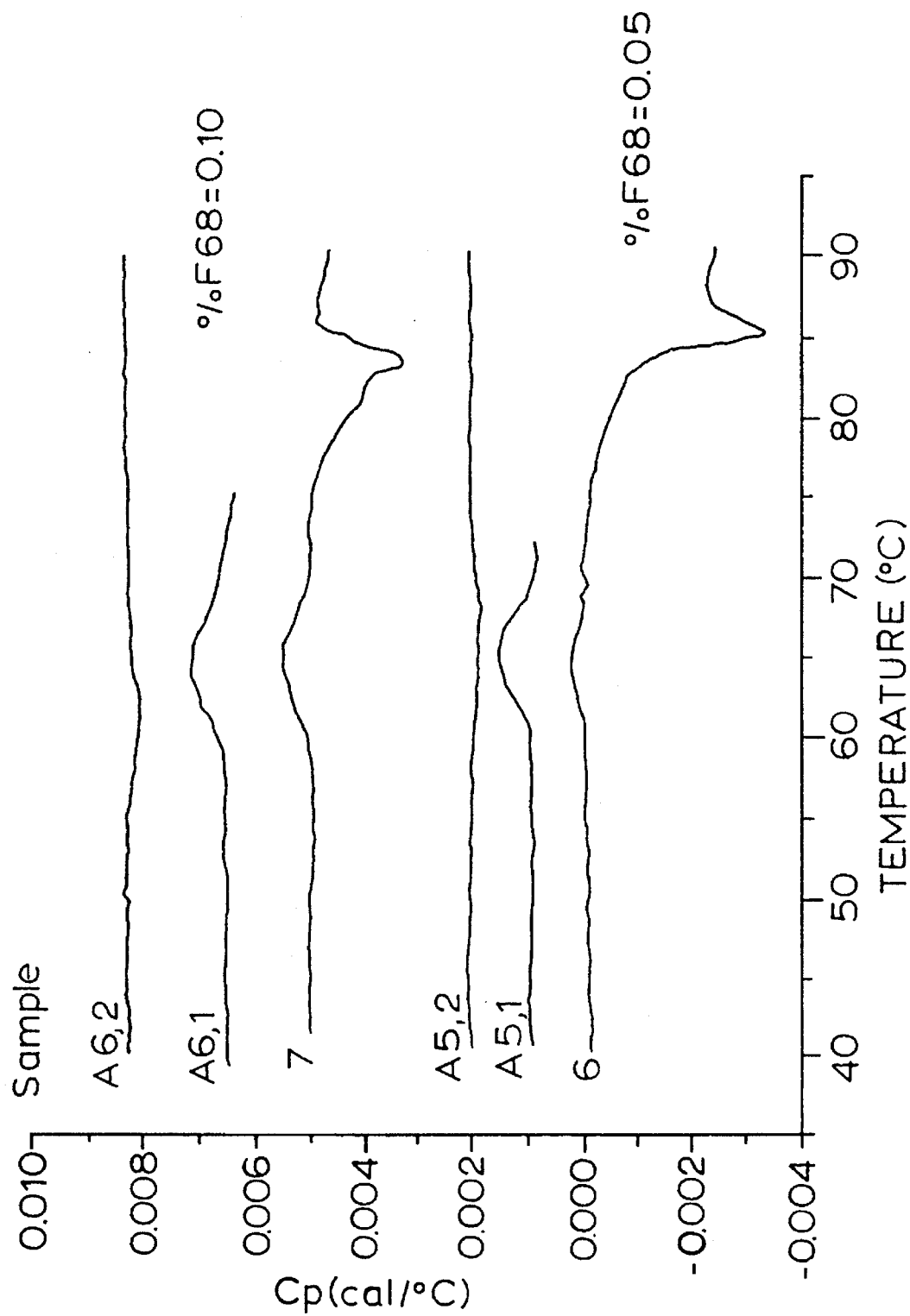
FIG. 10 is a set of graphs of differential scanning calorimetry results after a solution of $rBPI_{21}\Delta cys$ and poloxamer 188 (F68) was heated to a temperature higher than the denaturation/unfolding temperature but lower than the precipitation temperature, and then was cooled down for repeat scanning.

In addition to determining the melting behavior of rBPI$_{21}$Δcys, rescanning was done with rBPI$_{21}$Δcys formulations containing 0.05% and 0.10% poloxamer 188 to determine if unfolding is a reversible process. The temperature of the rBPI$_{21}$Δcys solution was first increased to 75° C. (temperature after denaturation/unfolding but before precipitation), then was cooled down for repeat scanning. FIG. 10 shows that the addition of poloxamer 188 to rBPI$_{21}$Δcys does not make unfolding reversible. Profiles A5, 1 and A6,1 show the scanning to 75° C., while profile A5,2 and A6,2 are repeat scanning after cooling the system from 75° C. If unfolding were a reversible process, 6 and 7 scan profiles would have been obtained.

The experimental results described above demonstrate that poloxamer surfactant alone is capable of stabilizing BPI-related polypeptides in solution and delaying the occurrence of precipitation by a mechanism that does not appear to involve modulation of the surface tension of the aqueous solution. This property is unique to poloxamer because other surfactants such as polysorbate 80 do not affect the precipitation phenomenon and do involve modulation of the surface tension of the aqueous solution.

EXAMPLE 7

The rate of rBPI$_{21}$Δcys precipitation during shipping was simulated in the laboratory by adjustment of the speed of the horizontal shaker. During five cycles of surface shipping, about 70% of the unformulated (surfactant free) rBPI$_{21}$Δcys precipitated. By varying the speed (rpm) of the flat-bed shaker, shake tests were then constituted such that 70 to 90% of unformulated rBPI$_{21}$Δcys subjected to the shake test precipitated. No rBPI$_{21}$Δcys was precipitated when the unformulated product was shaken on a flat bed shaker at 110 rpm or less for 18 hours at 4° C. Shaking at 140 pm (rather than at 150 rpm as in Examples 1 and 2) most closely simulated the agitation occurring during five cycles of surface transport. Changes in the flow dynamics of the liquid in the vial are substantially different at 140 rpm versus 150 rpm. Compositions including various concentrations of surfactant combinations were screened using the 140 rpm shake condition and the results obtained are set out in Table 4. It was determined that the optimal surfactant concentrations for protection from precipitation were 0.2% poloxamer 188 with 0.002% polysorbate 80 and 0.15% poloxamer 188 with 0.005% polysorbate 80.

TABLE 4

Summary of Shake Test at 140 rpm for rBPI$_{21}$ Δcys at 4° C.

| Poloxamer 188 (%) | PS80 (%) | Visual (see note) | Concentration by MA7C HPLC (mg/ml) | | |
|---|---|---|---|---|---|
| | | | Before | After | Loss (%) |
| 0.075 | 0.005 | 5 | 2.14 | 1.54 | 28 |
| | 0.010 | 4 | 2.10 | 1.56 | 26 |
| | 0.020 | 1 | 2.14 | 1.68 | 21 |
| 0.100 | 0.002 | 5 | 2.24 | 1.85 | 17 |
| | 0.005 | 4 | 2.14 | 1.85 | 14 |
| | 0.010 | 1 | 2.10 | 1.87 | 11 |
| | 0.020 | 1 | 2.13 | 1.94 | 9 |
| 0.150 | 0.002 | 3 | 2.19 | 1.92 | 12 |
| | 0.005 | 2 | 2.08 | 1.95 | 6 |
| | 0.010 | 1 | 2.19 | 1.94 | 11 |
| | 0.020 | 1 | 2.06 | 1.96 | 5 |
| 0.200 | 0.002 | 2 | 2.19 | 1.98 | 10 |
| | 0.005 | 1 | 2.19 | 1.95 | 11 |
| | 0.010 | 1 | 2.22 | 1.95 | 12 |

Note:
The scoring for visual observation is as follows:
1. Clear
2. Clear with few particulates
3. Slightly hazy
4. Hazy
5. Cloudy Based on the above data, a preferred formulation for 2 mg/mL rBPI$_{21}$Δcys to be stored at 4° C. would contain 5 mM citrate, 150 mM NaCl, pH 5.0, 0.2% poloxamer 188 and 0.002% polysorbate 80. An alternative formulation for 2 mg/ml rBPI$_{21}$Δcys to be stored at 4° C. would contain 5 mM citrate, 150 mM NaCl, pH 5.0, 0.15% poloxamer 188 and 0.005% polysorbate 80.

In summary, aggregation/precipitation is one of the major causes of protein instability and can occur when proteins at the air-liquid interface unfold and expose hydrophobic domains. If left unprotected, proteins self-associate through the interaction of the exposed hydrophobic domains, resulting in aggregation and/or precipitation. With the use of the surfactants and surfactant combinations of the invention, protein can be stabilized in two ways. First, exposed hydrophobic regions at the air-liquid interface are shielded by poloxamer surfactants. Second, additional stabilization can be provided by polysorbate surfactants through conventional modulation of the surface activity of the solution.

Numerous modifications and variations of the above-described invention are expected to occur to those of skill in the art. Accordingly, only such limitations as appear in the appended claims should be placed thereon.

What is claimed is:

1. A pharmaceutical composition comprising a bactericidal/permeability-increasing (BPI) protein or BPI fragment thereof, or a BPI analog of said bactericidal/permeability-increasing protein or BPI fragment, in combination with a polyoxypropylene-polyoxyethylene block copolymer (poloxamer) surfactant in a solubilizing/stabilizing concentration.

2. The pharmaceutical composition of claim 1 wherein the polyoxyporpylene-polyoxyethlene block copolymer (poloxamer) surfactant is poloxamer 188.

3. The pharmaceutical composition of claim 1 wherein the polyoxypropylene-polyoxyethylene block copolymer surfactant is present at said solubilizing/stabilizing concentration of from about 0.1% to about 0.2% by weight.

4. A pharmaceutical composition comprising a bactericidal/permeability-increasing (BPI) protein or BPI fragment thereof, or a BPI analog of said bactericidal/permeability-increasing protein or BPI fragment, in combination with a polyoxypropylene-polyoxyethylene block copolymer (poloxamer) surfactant for synergistically solubilizing/stabilizing said composition and a polyoxyethylene sorbitan fatty acid ester (polysorbate) surfactant.

5. The pharmaceutical composition of claim 4 wherein the polyoxypropylene-polyoxyethylene block copolymer (poloxamer) surfactant is poloxamer 188, and the polyoxyethylene sorbitan fatty acid ester (polysorbate) surfactant is polysorbate 80.

6. The pharmaceutical composition of claim 4 wherein the polyoxypropylene-polyoxyethylene block copolymer surfactant is present at a concentration of from about 0.1% to about 0.2% by weight, and the polyoxyethylene sorbitan fatty acid ester surfactant is present at a concentration of about 0.002% by weight.

\* \* \* \* \*